United States Patent
Blakemore et al.

(10) Patent No.: US 12,177,639 B2
(45) Date of Patent: Dec. 24, 2024

(54) WEARABLE ELECTRONIC DEVICE

(71) Applicant: Apple Inc., Cupertino, CA (US)

(72) Inventors: Andrea L. Blakemore, San Francisco, CA (US); Amit S. Barve, Santa Clara, CA (US); Donald L. Olmstead, Aptos, CA (US); Joshua A. Hoover, Boulder, CO (US); Samuel G. Smith, San Francisco, CA (US); Seulbi Kim, San Mateo, CA (US); James G. Griffin, II, Redwood City, CA (US); Linda D. Benavente-Notaro, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 85 days.

(21) Appl. No.: 17/680,102

(22) Filed: Feb. 24, 2022

(65) Prior Publication Data
US 2022/0240016 A1    Jul. 28, 2022

Related U.S. Application Data

(63) Continuation of application No. 16/452,926, filed on Jun. 26, 2019, now Pat. No. 11,290,818.
(Continued)

(51) Int. Cl.
*H04R 5/033* (2006.01)
*A61B 5/24* (2021.01)
(Continued)

(52) U.S. Cl.
CPC ............ *H04R 5/0335* (2013.01); *A61B 5/24* (2021.01); *A61F 9/04* (2013.01); *H04W 4/38* (2018.02); *H04R 2201/023* (2013.01)

(58) Field of Classification Search
None
See application file for complete search history.

(56) References Cited

U.S. PATENT DOCUMENTS

| | | | |
|---|---|---|---|
| 2,191,937 A | | 2/1940 | Low |
| 6,164,442 A | * | 12/2000 | Stravitz .................... A45C 3/02 221/45 |

(Continued)

OTHER PUBLICATIONS

Living Hinge, https://web.archive.org/web/20170101113948/https://en.wikipedia.org/wiki/Living_hinge (archived by the WayBack Machine on Jan. 11, 2017) (last accessed Jan. 4, 2024) (Year: 2017).*

*Primary Examiner* — Walter F Briney, III
(74) *Attorney, Agent, or Firm* — Treyz Law Group; Jason Tsai

(57) ABSTRACT

A wearable electronic device may be formed from a layer of fabric having opposing first and second ends. The ends may have first and second respective ear openings that receive a user's ears and may have speakers for playing audio. A soft central portion of the fabric between the ends may overlap the user's eyes. The wearable electronic device may have control circuitry that receives power from a power source. Sensors may be used to gather sensor information such as biometric sensor information. The sensors, control circuitry, and power source may be mounted in a stiff edge portion of the fabric. The stiff edge portion of the fabric may have an elongated strip shape and may extend along an upper edge of the central and the electronic device. Stiffener structures sandwiched between inner and outer layers of the fabric may be used to support speakers.

18 Claims, 9 Drawing Sheets

Related U.S. Application Data

(60) Provisional application No. 62/696,652, filed on Jul. 11, 2018.

(51) Int. Cl.
*A61F 9/04* (2006.01)
*H04W 4/38* (2018.01)

(56) References Cited

U.S. PATENT DOCUMENTS

| | | |
|---|---|---|
| 7,810,750 B2 | 10/2010 | Abreu |
| D775,260 S | 12/2016 | Gordon et al. |
| 10,500,098 B2 | 12/2019 | Mydell |
| 2004/0184635 A1 | 9/2004 | Natvig |
| 2008/0263749 A1 | 10/2008 | Leong et al. |
| 2009/0216070 A1 | 8/2009 | Hunt et al. |
| 2010/0122398 A1 | 5/2010 | Luciano |
| 2012/0124719 A1 | 5/2012 | Michlitsch et al. |
| 2013/0060306 A1 | 3/2013 | Colbauch |
| 2013/0117899 A1 | 5/2013 | Valentino |
| 2013/0216740 A1* | 8/2013 | Russell-Clarke ...... B21D 31/04 |
| | | 219/121.72 |
| 2013/0234823 A1 | 9/2013 | Kahn et al. |
| 2013/0303837 A1 | 11/2013 | Berka et al. |
| 2015/0000006 A1 | 1/2015 | Anderson |
| 2015/0018900 A1 | 1/2015 | Kirk et al. |
| 2017/0094399 A1* | 3/2017 | Chandramohan ...... H04R 1/345 |
| 2017/0135896 A1 | 5/2017 | Snow |
| 2017/0180838 A1* | 6/2017 | Hemesath ............. A45C 11/00 |
| 2017/0224951 A1 | 8/2017 | Weber et al. |
| 2017/0252533 A1* | 9/2017 | Genereux ................ A61F 9/04 |
| 2017/0264994 A1* | 9/2017 | Gordon ............... H04R 1/1091 |
| 2018/0021169 A1 | 1/2018 | Laghi |
| 2019/0110927 A1* | 4/2019 | Schwarz .................. A61F 9/04 |
| 2019/0149903 A1* | 5/2019 | Dowding-Young ...... A61F 9/04 |
| | | 381/74 |
| 2019/0298967 A1 | 10/2019 | Garcia Molina et al. |

* cited by examiner

WEARABLE ELECTRONIC DEVICE

This application is a continuation of patent application Ser. No. 16/452,926, filed Jun. 26, 2019, which claims the benefit of provisional patent application No. 62/696,652, filed Jul. 11, 2018, which are hereby incorporated by reference herein in their entireties.

FIELD

This relates generally to electronic devices, and, more particularly, to wearable electronic devices.

BACKGROUND

Electronic devices such as headphones may be worn by people who desire to listen to audio content. Headphones may not, however, be sufficiently comfortable for napping or wearing for long periods of time.

SUMMARY

A system may include a wearable electronic device and an associated portable electronic device or other host device such as a cellular telephone or computer. The wearable electronic device may gather biometric data from a user while playing audio for the user with speakers or other audio transfer components (e.g., bone conduction transducers that play audio for the user via bone conduction). Biometric data gathered with the wearable electronic device may be transferred to the host device so that reports on the user's biometric data may be displayed for the user.

The wearable electronic device may be formed from a layer of fabric. The fabric may have opposing first and second ends that are configured to receive a user's ears while the fabric covers the user's eyes. The ends may have ear openings with triangular edge portions that receive the user's ears. Tragus openings may be formed in the fabric to accommodate the tragus portions of the user's ears. A soft central portion of the fabric between the ends may overlap the user's eyes. Light sources may be placed within the central portion to provide illumination for the user's eyes.

The wearable electronic device may have control circuitry that receives power from a power source. Sensors may be used to gather sensor information such as biometric sensor information. The sensors, control circuitry, and power source may be mounted in a stiff edge portion of the fabric. The stiff edge portion of the fabric may have an elongated strip shape and may extend along an upper edge of the central portion of the fabric. Stiffener structures that are between inner and outer layers of the fabric may be used to support the speakers.

DETAILED DESCRIPTION

Items that are worn by a user may be formed from materials such as fabric. Fabric items may be light in weight and comfortable. For example, a wearable electronic device may be made of soft thin fabric that allows the device to be worn comfortably while users are sleeping on their sides and that does not press excessively against the users' faces. Sensors may be embedded in wearable electronic devices formed from fabric to monitor the operating environment of the wearable electronic devices and to make biometric measurements for users.

Figure 1:
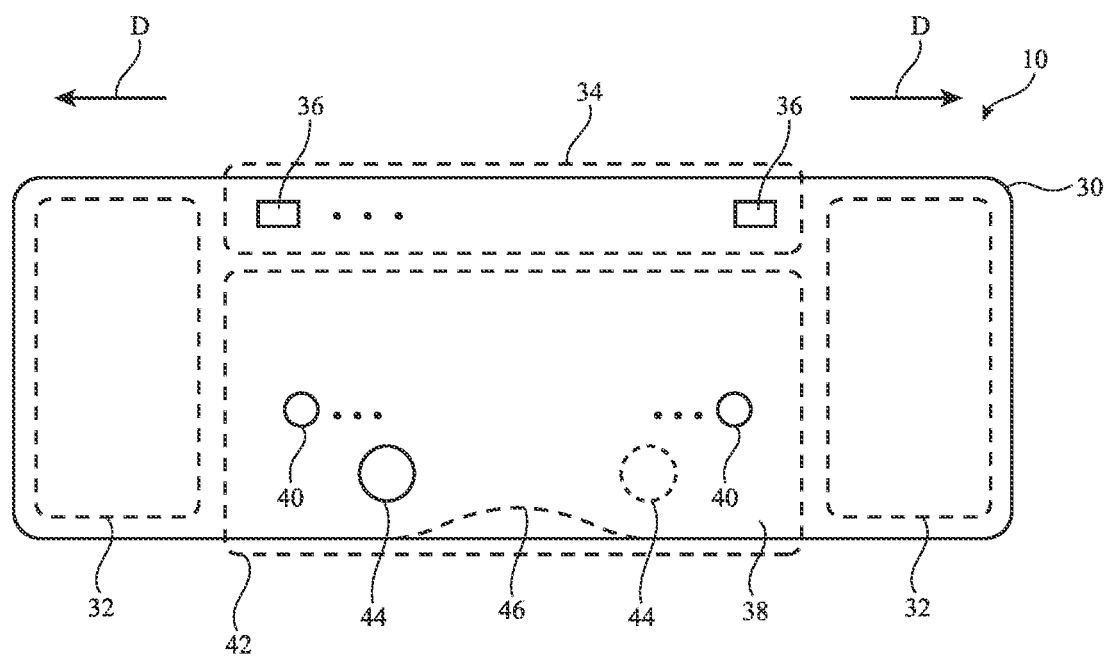
FIG. 1 is a front view of an illustrative wearable electronic device in accordance with an embodiment.

An illustrative wearable electronic device is shown in FIG. 1. As shown in FIG. 1, wearable electronic device 10 may include a body formed from fabric 30. Fabric 30 may include portions that have different properties. For example, fabric 30 may have reinforced portions that include stiffeners, folded (e.g., doubled-over) portions in which the stiffness of fabric 30 is selectively increased, portions that contain two or more layers of fabric that are coupled with adhesive and/or that have intervening layers of material, additional materials such as foam, polymer, fiber-composite materials, metal, adhesive, and/or other materials. Device 10 may include conductive strands or metal traces on a substrate such as a printed circuit or fabric layer that form signal paths for carrying electrical signals (e.g., wires in fabric 30 and/or attached to a surface of fabric 30). In some arrangements, locally softened or stiffened regions may be formed in device 10 (e.g., regions in which fabric 30 has a different construction such as a softer weave or knit, in which fabric 30 is formed from different numbers of layers of intertwined strands of material and/or stiffer and/or softer yarn, regions in which fabric 30 has a stiffer construction and/or includes polymer binder that stiffens fabric 30, etc.). Fabric 30 may also have portions with openings and/or other portions that have locally modified properties.

The outline of wearable electronic device 10 has an elongated rectangular shape in the example of FIG. 1, but other wearable electronic device shapes may be used, if desired. For example, the outline of wearable electronic device 10 may have rounded corners, curved edges along the top, bottom, left, and right sides of device 10, may have a combination of straight and curved edges, may have an oval shape, etc. With the illustrative elongated rectangular shape of FIG. 1, opposing left and right end portions 32 may have structures that engage a user's left and right ears, respectively. These structures may include ear openings in fabric 30 that are configured to receive the user's ears, hooks, straps, or other ear engagement structures. The central portion of wearable electronic device 10 between ends 32 may be placed across the front of a user's face to cover the user's eyes for rest or sleep. If desired, the outline of wearable electronic device 10 may include structures that help accommodate the user's facial features and enhance comfort. For example, foam may be formed in central portion 42, foam pads or other soft structures may be formed in areas such as areas 44 that rest to the left and right of the user's nose, etc. As another example, curved lower edge 46 may be formed to create additional space for the user's nose and thereby avoid applying too much pressure to the user's nose.

Electrical components may be included in device 10. For example, speakers or bone conduction transducers may be formed in end portions 32 to provide audio to a user. Electrical components may also be located in the central portion of fabric 30 between end portions 32. For example, light sources (e.g., light-emitting diodes or other light sources) may be located at locations such as locations 40 that are aligned with the positions of the user's eyes when device 10 is being worn on a user's face. Light sources such as these may be used to supply a user with light (e.g., to influence a user's sleep cycle as part of a light therapy regimen, to serve as an alarm, etc.). If desired, additional light blocking material may be placed over locations 40 and/or elsewhere in central portion (region) 42 (e.g., to help block ambient light in scenarios in which light sources are inactive or are omitted).

Fabric 30 may be stretchy, which allows fabric 30 to be tensioned in outward directions D when being worn by a user. To enhance comfort, it may be desirable to enhance the stiffness fabric 30 in a strip running along the upper edge of fabric 30 relative to other portions of fabric 30. For example, region 34 may have doubled-over portions of fabric 30 and/or other stiffening structures that make an elongated strip-shaped region that extends along the upper edge of fabric 30 stiffer than other, softer, portions of fabric such as the fabric of region 42. Wien device 10 is being worn on by a user, more of the tension (outward force in directions D) in fabric 30 will therefore be borne by the stiff upper edge portion of fabric 30 than in the softer regions such as region 42. This allows region 42 to be formed from fabric that is soft and comfortable, while ensuring that sufficient tension can be maintained across the width of fabric 30 so that device 10 is retained on a user's ears.

Because upper edge region 34 of fabric 30 may be stiffer than lower central portion 42, it may be desirable to locate rigid circuitry in region 34. For example, integrated circuits, packaged sensors, power sources, and other components may be formed in region 34 (see, e.g., illustrative electrical components 36). Circuitry such as components 36 may be interconnected using metal traces on one or more printed circuits (e.g., flexible printed circuits to which components 36 are mounted using solder, conductive adhesive, or other conductive materials), may be interconnected using wires (e.g., wires that have a central conductive strand of metal or other conductive material surrounded by an insulting jacket such as a coating of polymer), may be interconnected by conductive strands (monofilaments and/or multifilament yarn incorporated into fabric 30), or other signal path structures. Printed circuits, wires, and other signal path structures may, if desired, be located mostly in region 34 (e.g., so that these structures do not adversely affect the softness of region 42).

Figure 2:
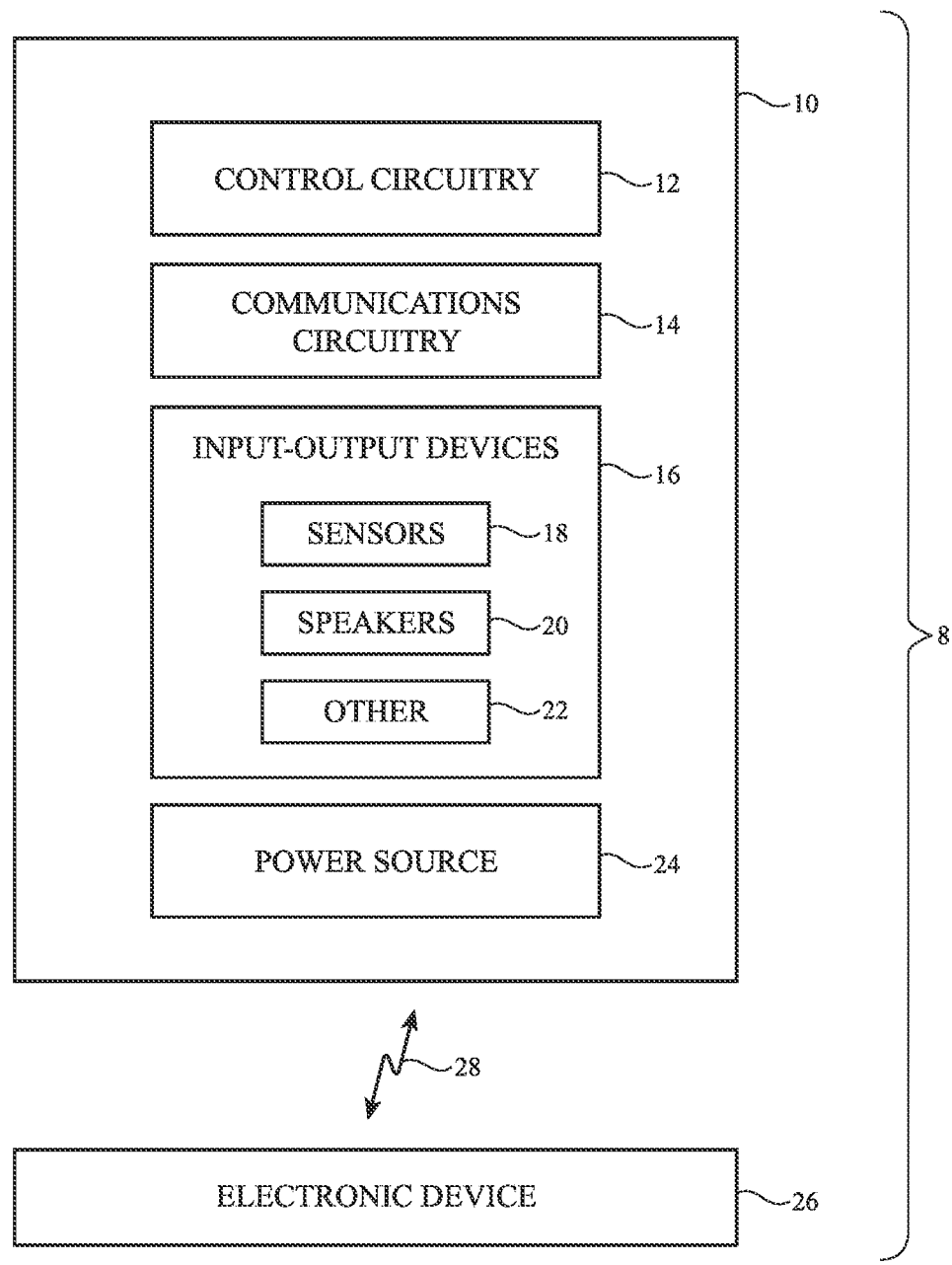
FIG. 2 is a schematic diagram of an illustrative system with a wearable electronic device in accordance with an embodiment.

A schematic diagram of an illustrative system that includes a wearable electronic device is shown in FIG. 2. Wearable electronic device 10 of system 8 may be used as a stand-alone device (e.g., a device that plays audio for a user and/or that performs other desired functions). If desired, system 8 may include one or more additional device such as electronic device 26. Devices such as device 26 may communicate with device 10 via wired and/or wireless communications paths (see, e.g., communications link 28). During communications, device 26 may provide device 10 with audio. For example, music and other audio may be streamed to device 10 from device 26 and/or audio files may be downloaded from device 26 to device 10 for immediate or future playback. Control information such as user-defined settings for system 8 and other control information may also be sent to device 10 from device 26 and/or sent from device 10 to device 26. Device 10 may use sensors and other circuitry to gather information on the user of device 10. This information may include, for example, biometric information (e.g., health data). During communications over link 28, biometric information and other information on the user of device 10 may be exchanged between device 10 and device 26. A user may, if desired, view biometric data that has been gathered in graphical format or other formats on a display in device 26.

Device 26 may be a laptop computer, tablet computer, desktop computer, cellular telephone, wristwatch, equipment embedded in a vehicle, building, or other system, a router or other network equipment, a battery case, or other electronic equipment. To form communications link 28, device 26 and wearable electronic device 10 may be coupled using a wired path (e.g., a cable and associated connectors that temporarily couple device 26 and wearable electronic device 10) and/or a wireless path. Wien coupled for communication, device 26 may provide information to wearable electronic device 10 (e.g., audio content, user settings, commands, etc.) and wearable electronic device 10 may provide information to device 26 (e.g., sensor data such as biometric measurements, etc.). Device 26 and device 10 may be coupled continuously or nearly continuously during operation (e.g., device 26 may be coupled to device 10 while a user is sleeping) or may be coupled more briefly (e.g., device 26 may be coupled to device 10 periodically when it is desired to transfer information across link 28). Wreless communications may be performed continuously (e.g., when streaming real-time audio) or intermittently. In some arrangements, a user may initiate the establishment of communications link 28 and may use a user interface in device 26 and/or in wearable electronic device 10 to manage the transfer of data and other operations in system 8. Configurations in which link 28 is formed automatically may also be used.

As shown in FIG. 2, device 10 may include control circuitry 12. Control circuitry 12 may include storage and processing circuitry for supporting the operation of device 10 and system 8. The storage and processing circuitry may include storage such as nonvolatile memory (e.g., flash memory or other electrically-programmable-read-only memory configured to form a solid state drive), volatile memory (e.g., static or dynamic random-access-memory), etc. Processing circuitry in the control circuitry may be used to gather input from sensors and other input devices and may be used to control output devices. The processing circuitry may be based on one or more microprocessors, microcontrollers, digital signal processors, baseband processors and other wireless communications circuits, power management units, audio chips, application specific integrated circuits, etc.

To support communications between device 10 and device 26 and/or to support communications between equipment in system 8 and external electronic equipment (e.g., over a network such as the internet), control circuitry 12 may have communications circuitry 14. Communications circuitry 14 may include antennas, radio-frequency transceiver circuitry, and other wireless communications circuitry and/or wired communications circuitry. Circuitry 14, which may sometimes be referred to as control circuitry and/or control and communications circuitry, may, for example, support bidirectional wireless communications between device 10 and device 26 over link 28 (e.g., a wireless local area network link, a near-field communications link, or other suitable wired or wireless communications link (e.g., a Bluetooth® link, a WFi® link, etc.). Device 10 may also include power circuits for transmitting and/or receiving wired and/or wireless power and may include batteries and/or capacitors to store power (see, e.g., power source 24).

Device 10 may include input output devices 16. Input-output devices 16 may be used in gathering user input, in gathering information on the environment surrounding the user, in gathering biometric measurements, and/or in providing a user with output. The input-output devices may include sensors such as sensors 18, speakers such as speakers 20 and other audio output devices such as bone condition transducers, and other devices 22.

Sensors 18 may include force sensors (e.g., strain gauges, capacitive force sensors, resistive force sensors, etc.), audio sensors such as microphones (e.g., microphones to monitor snorting, microphones for active noise cancellation, etc.), touch and/or proximity sensors such as capacitive sensors (e.g., capacitive touch sensors for gathering user touch input to adjust the operation of device 10, capacitive touch sensors for determining when device 10 is being worn against the skin of a user or is not being worn, etc.), optical sensors such as optical sensors that emit and detect light, and/or other touch sensors and/or proximity sensors, monochromatic and color ambient light sensors, image sensors, sensors for detecting position, orientation, and/or motion (e.g., accelerometers, magnetic sensors such as compass sensors, gyroscopes, and/or inertial measurement units that contain some or all of these sensors), biometric sensors such as muscle activity sensors (EMG) for measuring eye muscle contractions and other muscle contractions, eye motion sensors, blood pressure sensors, heart rate sensors, electrocardiography (ECG) sensors for measuring heart activity, photoplethysmography (PPG) sensors for sensing the rate of blood flow using light, and electroencephalograph (EEG) sensors for measuring electrical activity in the user's brain, pressure sensors (e.g., force sensors that can detect pressure on the side of a user's head when the user is resting against a pillow), humidity sensors, temperature sensors, moisture sensors, and/or other sensors. In some arrangements, device 10 may use sensors such as sensors 18 and/or other input-output devices such as input-output devices 16 to gather user input (e.g., buttons may be used to gather button press input, touch sensors overlapping displays can be used for gathering user touch screen input, touch pads may be used in gathering touch input, microphones may be used for gathering audio input, accelerometers may be used in monitoring when a finger contacts an input surface and may therefore be used to gather finger press input, etc.).

Device 10 may include speakers 20 or other audio output components for presenting audio to a user. Earbud-shaped portions of device 10 or other structures may be used to help locate speakers 20 (or other audio output devices such as bone conduction transducers) in alignment with the user's ears (e.g., in and/or aligned with the user's concha). During operation of device 10, audio may be provided directly by control circuitry 12 (e.g., audio stored in circuitry 12 may be played back for a user with speakers 20) and/or audio may be provided from remote equipment (e.g., circuitry 12 may use communications circuitry 14 to receive audio from device 26, which circuitry 12 may play for a user via speakers 20).

Device 10 may also include other devices 22 such as haptic output devices, light-emitting devices such as light-emitting diodes, lasers, electroluminescent devices, and lamps (e.g., light sources located in locations such as locations 40 of FIG. 1), displays, wireless power components (e.g., inductive power coils and rectifiers for receiving wireless power, and/or wireless power transmitting circuitry), heating devices (e.g., ohmic heaters, Peltier effect devices, etc.), cooling devices (e.g., Peltier effect devices), and/or other electrical components.

Devices such as device 26 in system 10 may include components such as control circuitry 12, communications circuitry 14, input-output devices 16, power source 24, and/or other components.

Figure 3:
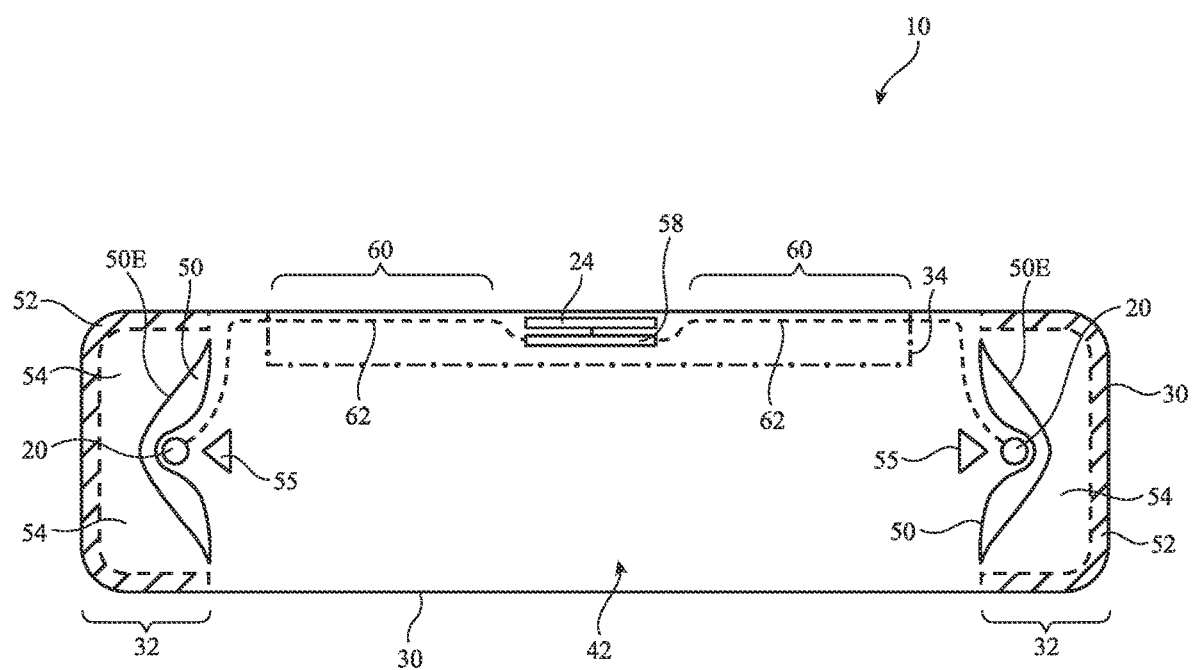
FIG. 3 is a front view of an illustrative wearable electronic device with ear holes and speakers in accordance with an embodiment.

An illustrative configuration for wearable electronic device 10 is shown in FIG. 3. As shown in FIG. 3, end portions 32 of fabric 30 may include openings such as ear openings 50 that are configured to receive the ears of a user. Ear openings 50 may have triangular outer edges 50E, which allow device 10 to accommodate a wide range of ear shapes and head sizes while maintaining a desired amount of tension in fabric 30. In this way, fabric 30 can be gently stretched across a user's face and held in place by the resulting tension from the user's ears. Because device 10 may be worn across a users face during sleep, device 10 may sometimes be referred to as a sleep mask.

Speakers 20 may be mounted adjacent to ear openings 50 in locations that serve to align speakers 20 with the user's ears (e.g., the user's conchae). Fabric 30 may, if desired, have openings such as tragus openings 55. Tragus openings 55 may allow a user's tragi to protrude through fabric 30 as device 10 is being worn by the user. This may help reduce pressure from fabric 30 on the user's ears and enhance the comfort of device 10. Uncomfortable ear pressure may also be alleviated by incorporating soft material such as foam into regions 54 adjacent to ear openings 50 and/or into central portion 42.

Regions 54 may be located between ear openings 50 and adjacent peripheral edge portions of device 10 such as edge portions 52. Peripheral edge portions 52 in ends 32 may be locally stiffened using two layers of fabric 30 bonded together using adhesive or other stiffening structures. Stiffening structures may also be formed in device 10 that help to support and locate speakers 20 in alignment with a user's ears.

As shown in FIG. 3, speakers 20 may be coupled to electrical components such as electrical components 58 using signal paths 62 (e.g., so that audio signals may be provided to speakers 20). Component(s) 58 (see, e.g., components 36 of FIG. 1) may include integrated circuits (e.g., audio drivers), wires, and other circuitry (see, e.g., control circuitry 12, communications circuitry 14, and input-output devices 16 of FIG. 2). Power for the circuitry of components 58 may be supplied by power source 24 (e.g., a capacitor, battery, or other source of power). Power source 24 and/or associated connectors for coupling to a power supply cable and/or wireless power receiving circuitry may, if desired, be accommodated by forming a protruding portion of fabric 30 along the upper edge of device 10 (as an example).

Components 58 may be formed in region 34, which may be locally stiffened. For example, region 34 may be a strip-shaped region extending along the upper edge of fabric 30 that is stiffened relative to other portions of device 10 such as the portions of device 10 in region 42 using folded fabric, other configurations with multiple fabric layers, arrangements in which a polymer layer, a fiber-composite layer such as a fiberglass layer, a metal layer, or other structures serve to stiffen device 10 in region 34. If desired, components 58 may be formed in regions such as regions 60 (e.g., regions 60 may include sensors 18 and other components).

Figure 4:
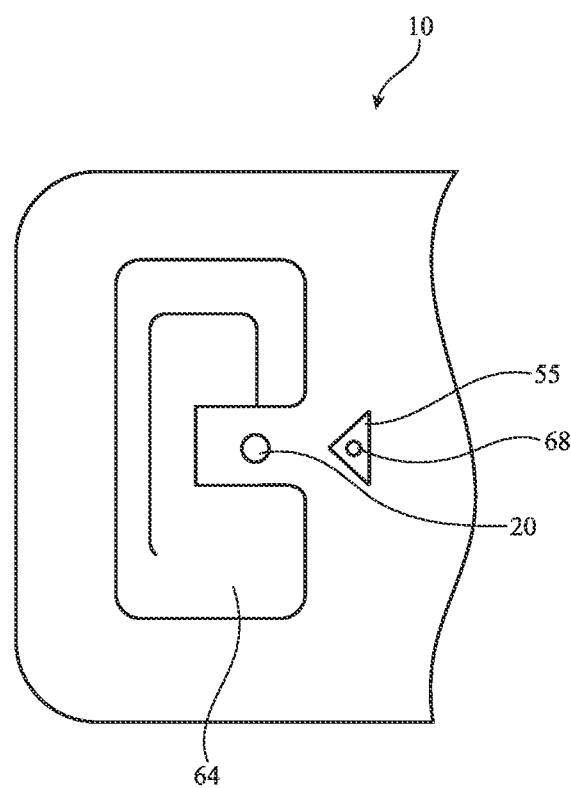
FIG. 4 is a diagram of a user's ear on which a portion of a wearable electronic device is being worn in accordance with an embodiment.

FIG. 4 is a diagram of an end portion of device 10 showing how ear opening 50 of fabric 30 may fit over a user's ear (ear 64) to hold an end of device 10 in place. In this position, tragus opening 55 is aligned with the user's tragus 68 so that undesired fabric pressure on tragus 68 is avoided.

Figure 5:
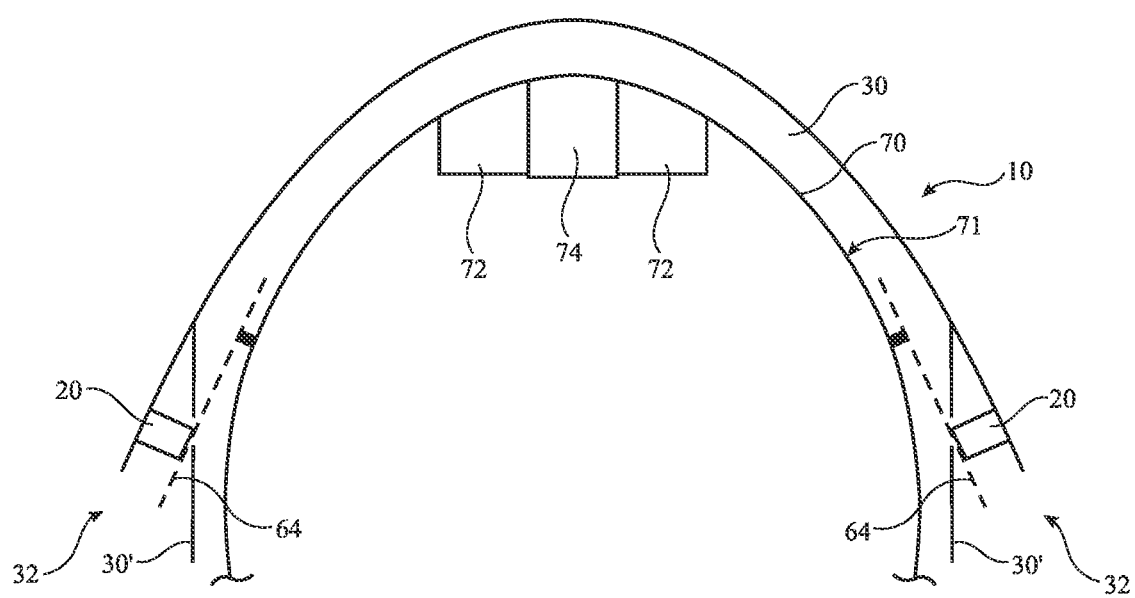
FIG. 5 is a top view of a head of a user wearing an illustrative wearable electronic device in accordance with an embodiment.

FIG. 5 is a top view of user 71 and device 10 showing how device 10 may be worn by user 71. As shown in FIG. 5, device 10 may stretch across the face of user's head 70, covering the user's eyes 72. Device 10 may also cover some or all of the user's nose 74. By blocking eyes 72, device 10 may allow user 71 to sleep or rest even when ambient lighting conditions are bright. To attach device 10 to head 70, openings 50 at ends 32 of device 10 may be placed over the user's ears 64 (e.g., so that portions 30' of fabric at the outermost edges of fabric 30 are located behind ears 64). In this position, the fabric of device 10 may stretch slightly to create tension in device 10 that helps secure device 10 to ears 64 and hold device 10 over the user's face (e.g., over eyes 72).

To allow fabric 30 to stretch, fabric 30 may include strands of material that can accommodate stretching without becoming damaged (e.g., spandex, polyester, other stretchable materials, or combinations of these materials). Fabric 30 may also include less stretchy strands (e.g., fabric 30 may include strands of acrylic or nylon to add strength). Fabric 30 may be formed by any suitable fabric construction technique (weaving, knitting, braiding, etc.) and may include one or more intertwined sublayers. The density of fabric 30 may be sufficient to block bright light from eyes 72 and/or additional layers of material (e.g., an opaque polymer layer, etc.) may be included in device 10 to ensure that device 10 blocks light sufficiently.

Figure 6:
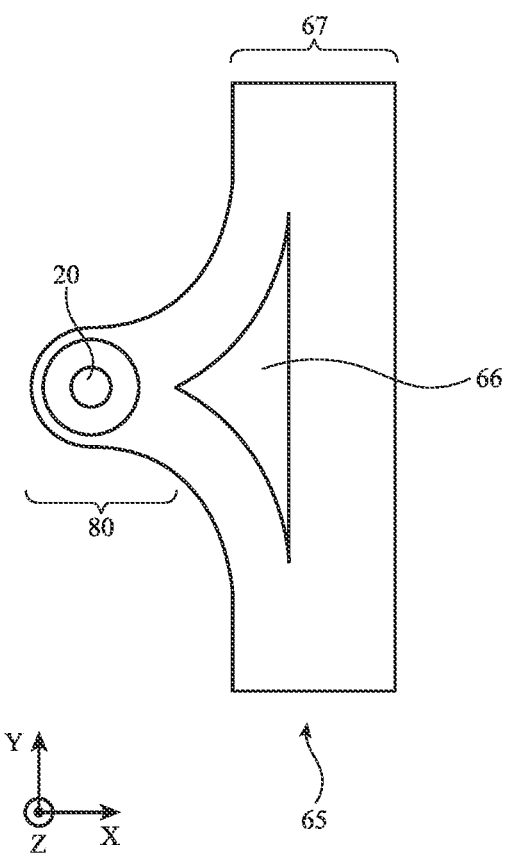
FIG. 6 is a side view of an illustrative stiffener for supporting a speaker in a wearable electronic device in accordance with an embodiment.

FIG. 6 is a diagram of an illustrative stiffener of the type that may be incorporated into each end 32 of device 10 (e.g., so that there are separate first and second stiffeners in device 10 separated by a thin soft fabric layer in central portion 42). As shown in FIG. 6, stiffener 65 may have a diving board shape characterized by a protruding portion such as protruding portion 80 that protrudes from a main portion such as main portion 67. Protruding portion 80 may be flat (e.g., portion 80 may lie in the same plane as main portion 67) or protruding portion 80 may curve toward the user's head (e.g., upward from the page and therefore upward from the plane in which main portion 67 lies in the origination of FIG. 6). By curving portion 80, speaker 20 may be biased towards and into the user's concha when device 10 is worn on the user's head. Tragus opening 66 may pass through stiffener 65 to help accommodate a user's tragus. Stiffener 65 may be sandwiched between inner and outer layers of fabric 30 and/or may otherwise be incorporated into device 10.

Figure 7:
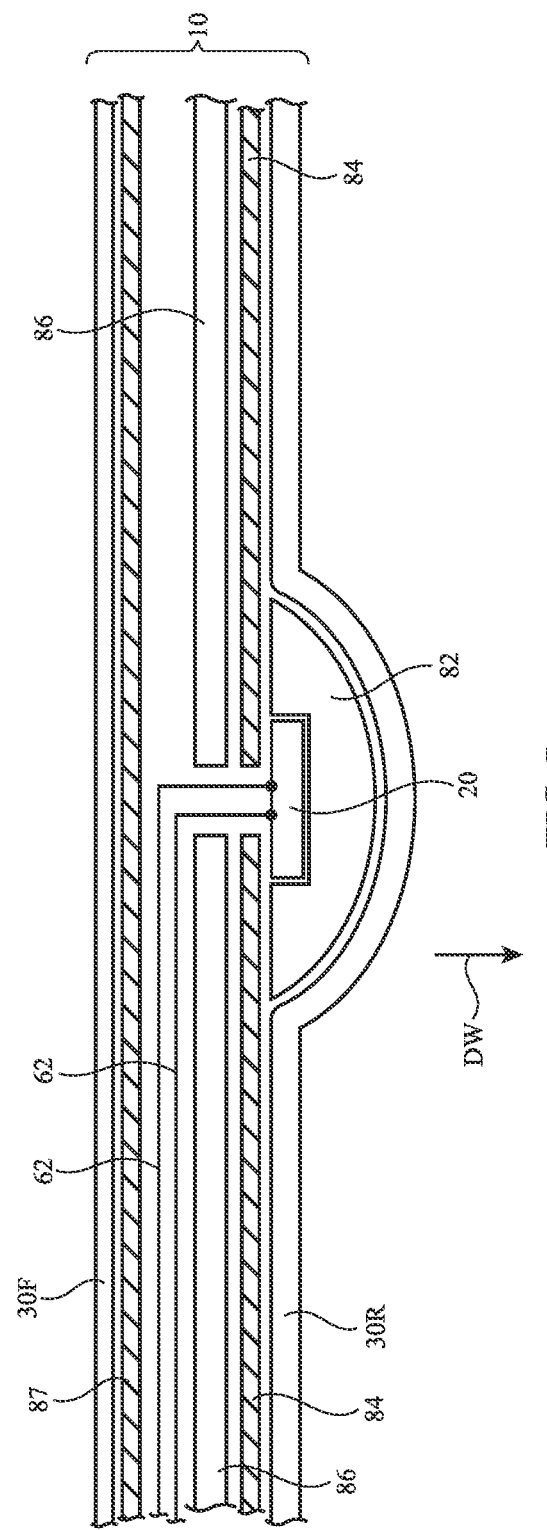
FIG. 7 is a cross-sectional side view of an illustrative speaker in a wearable electronic device in accordance with an embodiment.

FIG. 7 is a cross-sectional side view of a portion of device 10 in the vicinity of a left or right speaker. As shown in FIG. 7, fabric 30 of device 10 may include outwardly facing fabric such as front fabric layer 30F on the front face of device 10 and may include inwardly facing fabric such as rear fabric layer 30R on the opposing rear face of device 10. Wien being worn on a head of a user, the fabric of layer 30F, which may sometimes be referred to as an outer fabric layer, may face outwardly and may be viewed by people in the vicinity of the user, whereas the fabric of layer 30R, which may sometimes be referred to as an inner fabric layer, may face inwardly and may rest against the skin of the user's face.

An earbud-shaped speaker structure may be formed by placing a soft earbud member such as foam member 82 over speaker 20. Foam member 82 may have a domed shape. The presence of foam member 82 may allow for relative movement between speaker 20 and a stiffener overlapped by speaker 20 (e.g., internal stiffening layer 86) and to improve comfort. Member 82 may have an opening to accommodate sound and/or may be formed from open-cell foam that allows sound to pass. Fabric layer 30R may cover foam 82. Layer 30R may be sufficiently thin to allow sound from speaker 20 to pass to the user's ear and/or an opening may be formed in layer 30R in alignment with speaker 20. Adhesive 84 may attach fabric layer 30R to internal stiffening layer 86. Stiffening layer 86 may be formed from a layer of material that is stiffer than fabric 30 (e.g., stiffer than fabric layer 30F and stiffer than fabric layer 30R). For example, stiffening layer 86 may be formed from a fiber composite material such as fiberglass and/or may be formed from other stiffening structures such as a layer of polymer without embedded fibers, stiff fabric, etc. Stiffening layer 86 may have a diving board shape or may have other suitable shapes and may form a stiffener such as stiffener 65 of FIG. 6. An opening in stiffener layer 86 may allow wires or other signal paths 62 to convey audio signals to speaker 20. Adhesive layer 87 may be interposed between stiffener layer 86 and fabric layer 30F to attach fabric layer 30F to stiffener layer 86. Adhesive layer 87 and/or other attachment mechanisms (e.g., solder, fasteners, etc.) may also be used to attach speaker 20 to stiffener layer 86. Stiffener layer 86 may be planar as shown in FIG. 7 or a protruding diving board stiffener formed from layer 86 may be bent downwards towards the user's ear in direction DW.

Figure 8:
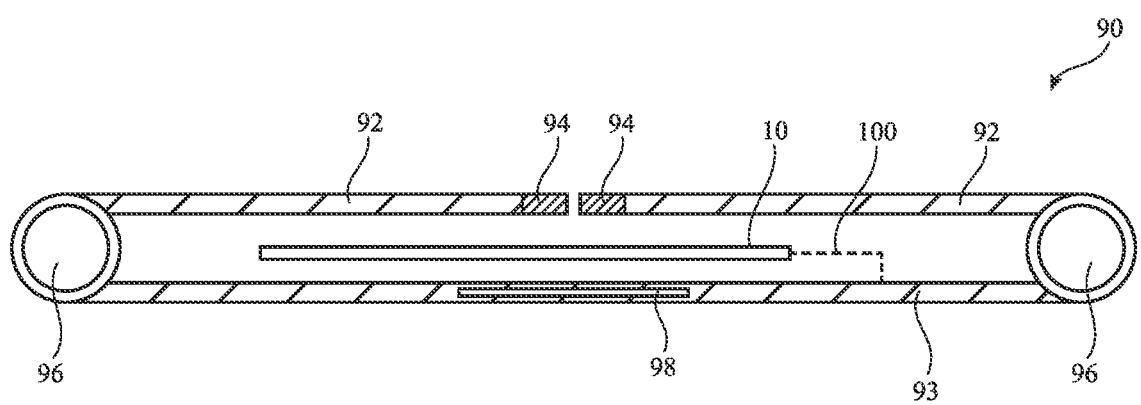
FIG. 8 is a cross-sectional side view of an illustrative case for a wearable electronic device in accordance with an embodiment.

FIG. 8 is a cross-sectional side view of an illustrative enclosure for device 10. As shown in FIG. 8, enclosure 90, which may sometimes be referred to as a battery case, cover, holder, etc., may have hinges such as hinges 96 that allow front wall portions 92 to rotate relative to rear wall portion 93. Clasp 94 may have magnetic structures or mechanical engagement structures to selectively hold portions 92 in a closed position. If desired, hinges 96 may be formed from flexible enclosure wall structures. The walls of enclosure 90 may be formed from fabric, leather, polymer, metal, other materials, or combinations of these materials. Enclosure 90 may include a battery such as battery 98. After battery 98 is charged using a wired connection or wireless power circuitry that receives wireless power from a wireless power source such as a wireless power charging mat, battery 98 may supply power to device 10 (e.g., to recharge a battery or other power source in device 10). For example, power may be supplied from battery 98 to device 10 using a wired path such as wired path 100. Wreless power arrangements in which enclosure 90 wirelessly transmits power to power source 24 of device 10 may also be used.

During the operations of system 8, user input may be gathered. For example, button press input, touch sensor input, voice command input, force sensor input, and/or other input may be gathered using input-output devices 16 and/or input-output devices in external equipment such as device 26. The user input may include commands that adjust media playback (e.g., commands such as play, rewind, fast forward, skip track, stop, pause, volume up, volume down, etc.). These media playback commands may be used to adjust the volume used by control circuitry 12 when playing audio for the user with speakers 20 and/or other audio playback settings.

The user input may also include commands to start or stop sensor measurements. If, as an example, a user supplies input that directs system 8 to begin a sleep cycle routine, audio may be played from speakers 20 while sensors 18 gather biometric data and other sensor measurements. Biometric data may also be gathered while speakers 20 are inactive or audio may be placed without gathering biometric data. Audio for device 10 may be white noise or other sleep-oriented audio tracks (wave sounds, etc.), may be songs or other music, may include spoken words, or may be any other suitable audio content.

Sensor data can be conveyed from device 10 to device 26 after the user's sleep cycle has completed (e.g., in response to a user supplying a stop command) or can be conveyed periodically or continuously between device 10 and device 26 during the user's sleep cycle. If desired, light from light sources aligned with the user's eyes can be provided at appropriate times (e.g., when awakening the user from sleep in the morning at a predetermined alarm time, at times that are chosen to help the user adapt to a new time zone, etc.). Portions of device 10 may also be heated or cooled.

Visual feedback, audio feedback, and/or haptic feedback may be provided to the user of system 8 during operation. For example, a touch sensitive display on device 26 may display selectable on-screen options (e.g., a "start" button, a "stop" button, a "snooze" button, a "transfer data" button, a "display sleep report" button, an "adjust options" button, or other selectable options. System 8 may take suitable action in response to user input provide when a user touches a displayed on-screen option or otherwise provides system 8 with a command. For example, device 10 may adjust settings, may initiate or stop data gathering, may play appropriate audio, provide appropriate light output, heat output, cooling output, haptic output, and/or other output while gathering user input, environmental sensor measurements, biometric sensor measurements, and/or other input and may provide confirmatory messages ("monitoring your sleep," "alarm snoozed," "recording paused," etc.). Messages and other output may be displayed by a display in device 26, and/or may be provided as audible messages and/or tactile output.

Figure 9:
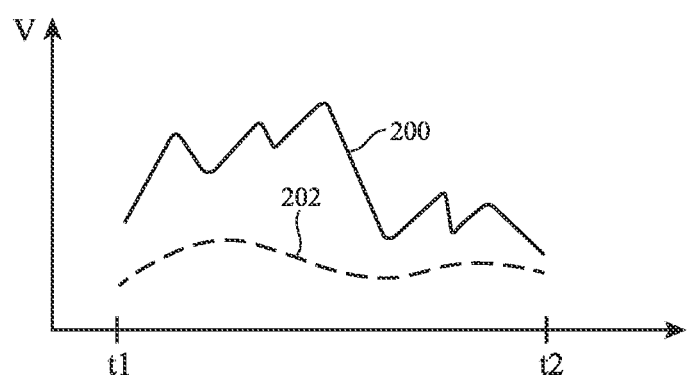
FIG. 9 is a graph of illustrative data that may be gathered with a wearable electronic device and displayed for a user on an associated electronic device in accordance with an embodiment.

Following the recording of data with sensors 18 during a sleep cycle, system 8 may provide measurement results to the user. For example, sensor data conveyed from device 10 to device 26 may be displayed using graphs such as the illustrative graph of FIG. 9. In the illustrative graph of FIG. 9, time t1 indicates the start time for use of device 10 and time t2 indicates the stop time for use of device 10. \arable electronic device information (e.g., curve 200 and curve 202) has been plotted as a function of time. In this example, value(s) V represents the magnitude of each plotted parameter during use of device 10. These parameters may include measured biometric information such as heart rate, blood flow, eye movement amount, respiration rate, accelerometer output (indicating body movement and/or respiration rate), muscle activity, EEG information, ECG information, body temperature, etc. Additional system information (e.g., ambient noise level, audio playback state, light source output level, etc.) may also be plotted on the display of device 26 and analyzed when generating sleep measurement results for a user. Sleep measurements and associated parameters may be analyzed by device 10 and/or device 26 and the results of the analysis may be presented to the user on the display of device 26. For example, the amount of body motion of the user may be analyzed to categorize the motion level as being low, medium, or high. If desired, raw and analyzed information may be analyzed and/or stored online (e.g., using one or more devices such as device 26 that are coupled to system 8 through a network such as the internet).

The foregoing is merely illustrative and various modifications can be made to the described embodiments. The foregoing embodiments may be implemented individually or in any combination.

What is claimed is:

1. A wearable electronic device configured to be worn by a user, comprising:
   a central portion having light-blocking fabric;
   a right speaker disposed in a right end coupled to a first end of the central portion; and
   a left speaker disposed in a left end coupled to a second end of the central portion, wherein:
   the right end has a first portion configured to bias the right speaker towards and into a right ear concha of the user and a second portion configured to receive a right tragus of the user; and
   the left end has a first portion configured to bias the left speaker towards and into a left ear concha of the user and a second part configured to receive a left tragus of the user.

2. The wearable electronic device of claim 1, wherein:
   the second portion of the right end comprises a right tragus opening configured to accommodate the right tragus of the user; and
   the second portion of the left end comprises a left tragus opening configured to accommodate the left tragus of the user.

3. The wearable electronic device of claim 1, wherein:
   the second portion of the right end comprises a right tragus opening in a first stiffener configured to accommodate the right tragus of the user; and
   the second portion of the left end comprises a left tragus opening in a second stiffener configured to accommodate the left tragus of the user.

4. The wearable electronic device of claim 1, wherein:
   the second portion of the right end comprises fabric with a right tragus opening configured to accommodate the right tragus of the user; and
   the second portion of the left end comprises fabric with a left tragus opening configured to accommodate the left tragus of the user.

5. The wearable electronic device of claim 1, wherein:
   the second portion of the right end forms a main portion of a first stiffener;
   the first portion of the right end forms a protruding portion that protrudes from the main portion of the first stiffener;
   the second portion of the left end forms a main portion of a second stiffener; and
   the first portion of the left end forms a protruding portion that protrudes from the main portion of the second stiffener.

6. The wearable electronic device of claim 5, wherein:
   the main portion of the first stiffener and the protruding portion of the first stiffener lie in the same plane; and
   the main portion of the second stiffener and the protruding portion of the second stiffener lie in the same plane.

7. The wearable electronic device of claim 5, wherein:
   the main portion of the first stiffener lies in a first plane and the protruding portion of the first stiffener curves away from the first plane; and the main portion of the second stiffener lies in a second plane and the protruding portion of the second stiffener curves away from the second plane.

8. The wearable electronic device of claim 1, further comprising one or more integrated circuits mounted on a locally stiffened region in the central portion.

9. The wearable electronic device of claim 8, wherein the locally stiffened region extends along a peripheral edge of the central portion.

10. An enclosure having a rear wall portion configured to receive the wearable electronic device of claim 1 and having one or more wall portions coupled to the rear wall portion via one or more hinges.

11. A system comprising:
a wearable electronic device having fabric, speakers inside the fabric, tragus openings configured to accommodate a left tragus and a right tragus, and a sensor configured to gather health data; and
an enclosure having
a first wall portion configured to receive the wearable electronic device, and
a second wall portion that rotates relative to the first wall portion and that at least partially covers the wearable electronic device in a closed position.

12. The system of claim 11, wherein the wearable electronic device comprises a sleep mask having light sources.

13. The system of claim 11, wherein the tragus openings comprise:
a right tragus opening in the fabric or in a stiffener; and
a left tragus opening in the fabric or in a stiffener.

14. The system of claim 13, wherein the wearable electronic device further comprises:
one or more integrated circuits mounted on a locally stiffened portion extending between the left and right tragus openings.

15. The system of claim 11, wherein the enclosure further comprises a third wall portion that rotates relative to the first wall portion and that at least partially covers the wearable electronic device in the closed position.

16. The system of claim 15, wherein the enclosure further comprises:
a first hinge about which the second wall portion rotates relative to the first wall portion; and
a second hinge about which the third wall portion rotates relative to the first wall portion.

17. The system of claim 15, wherein:
the second wall portion comprises a first end attached to the first wall portion and a second end having a first magnetic structure; and
the third wall portion comprises a first end attached to the first wall portion and a second end having a second magnetic structure configured to magnetically attract the first magnetic structure.

18. The system of claim 11, wherein the enclosure further comprises a battery for charging the wearable electronic device.

* * * * *